Figure 1:
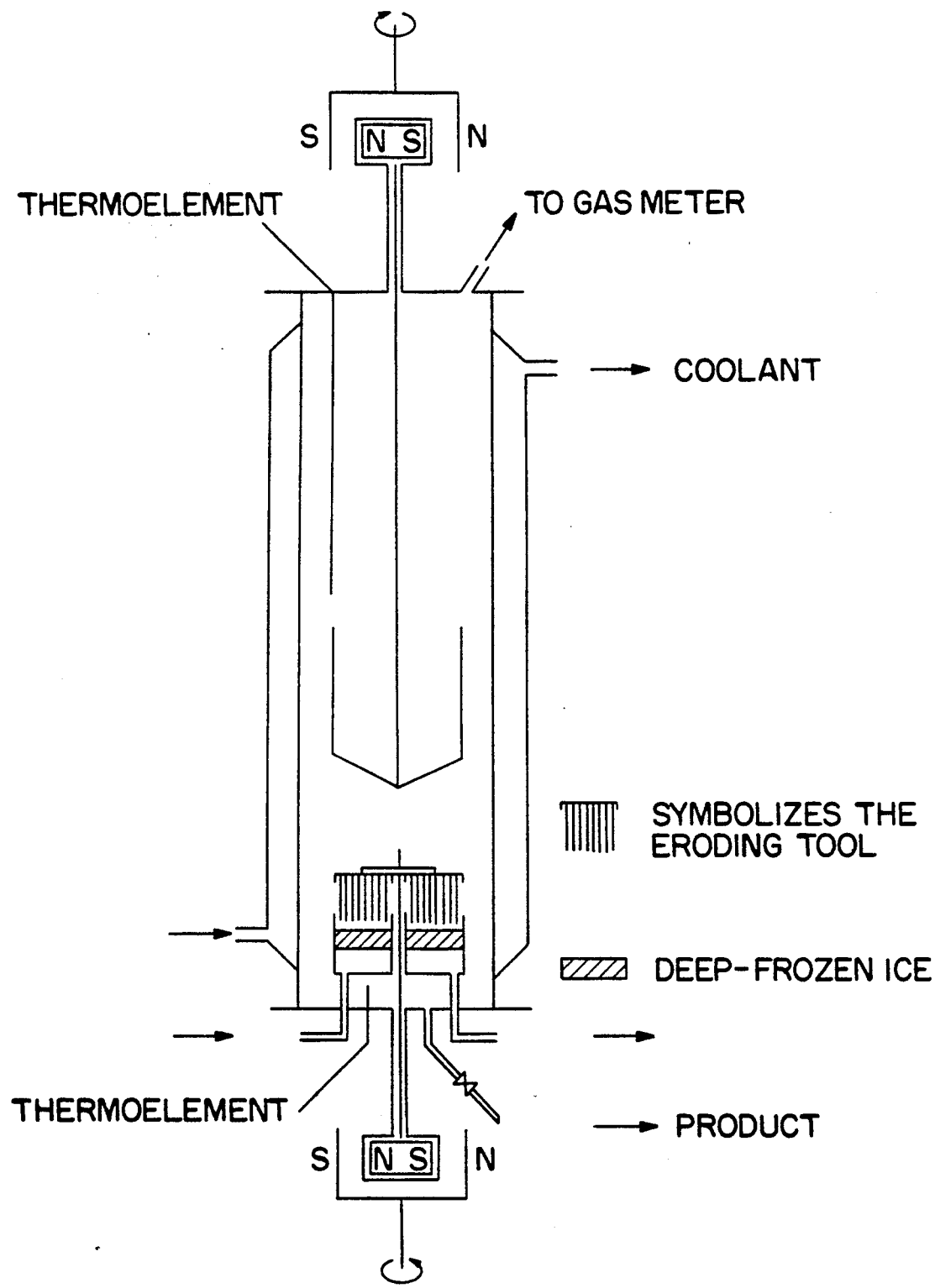

United States Patent [19]

Sinn et al.

[11] Patent Number: 5,087,713
[45] Date of Patent: Feb. 11, 1992

[54] PROCESS FOR PRODUCING ALUMINUM OXANES, IN PARTICULAR METHYLALUMINUM OXANE, FROM WATER AND ORGANOALUMINUM COMPOUNDS, IN PARTICULAR TRIMETHYLALUMINUM, IN INERT HYDROCARBONS

[75] Inventors: Hansjoerg Sinn, Norderstedt; Dieter Clausnitzer, Reinbek; Hergen Winter, Quickborn, all of Fed. Rep. of Germany

[73] Assignee: Schering AG, Bergkamen, Fed. Rep. of Germany

[21] Appl. No.: 469,579

[22] PCT Filed: Sep. 19, 1988

[86] PCT No.: PCT/EP88/00864
§ 371 Date: Mar. 20, 1990
§ 102(e) Date: Mar. 20, 1990

[87] PCT Pub. No.: WO89/02434
PCT Pub. Date: Mar. 23, 1989

[30] Foreign Application Priority Data
Sep. 20, 1987 [DE] Fed. Rep. of Germany ....... 3731665

[51] Int. Cl.$^5$ ............................................. C07F 5/06
[52] U.S. Cl. .................................... 556/179; 556/175; 556/178; 556/187
[58] Field of Search ................ 556/179, 178, 175, 187

[56] References Cited

U.S. PATENT DOCUMENTS

| 4,730,071 | 3/1988 | Schoenthal et al. | 556/179 |
| 4,730,072 | 3/1988 | Schoenthal et al. | 556/179 |

FOREIGN PATENT DOCUMENTS

| 0208561A3 | 1/1987 | European Pat. Off. |
| 0247695 | 3/1988 | European Pat. Off. |
| 0258924A2 | 3/1988 | European Pat. Off. |
| 102562 | 5/1979 | Poland |

OTHER PUBLICATIONS

Boleslawski et al., *J. Organomet. Chem.* 1983, 255(3), 269-78 (Chem. Abs. 100:13918ZN).

*Primary Examiner*—Jose G. Dees
*Assistant Examiner*—Porfirio Nazario
*Attorney, Agent, or Firm*—Curtis, Morris & Safford

[57] ABSTRACT

A process is disclosed for producing aluminum oxane by subjecting frozen water in a solution of trialkylaluminum in hydrocarbons to erosive action. In particular, a process is disclosed for producing methylaluminum oxane which is characterized in that frozen water in a solution of trimethylaluminum in hydrocarbons is subjected to erosive action which is exerted by mechanical action or by one or more intensive liquid jets of the reaction solution sweeping over the surface of the frozen water.

20 Claims, 1 Drawing Sheet

PROCESS FOR PRODUCING ALUMINUM OXANES, IN PARTICULAR METHYLALUMINUM OXANE, FROM WATER AND ORGANOALUMINUM COMPOUNDS, IN PARTICULAR TRIMETHYLALUMINUM, IN INERT HYDROCARBONS

Aluminum oxanes are formed during the controlled reaction of aluminum alkyls with water. A typical characteristic is the linking of two aluminum atoms which still carry organic groups through an oxygen atom. The first representative of the aluminum oxanes is oxo-bis-dialkylaluminum or tetraalkyldialuminum oxide. Its isolation and characterization, particularly with methyl as the alkyl group, are not known to this day.

As a rule, the reaction between water and aluminum alkyls results in complete hydrolysis, in other words, in the formation of aluminum oxide, often with violent reaction and even flame formation.

A number of different methods have been developed for the cautious, controlled and incomplete reaction between water and aluminum alkyls. They have been published by (1) E. J. Vandenberg, J. Pol. Sci. 47 (1960) 485; (2) N. N. Korneev, A. F. Popov, E. J. Larikov, A. F. Zhigach and G. B. Sakharovskaya, J. Gen. Chem. USSR 34 (1964) 3425; (3) A. Storr, K. Jones and A. W. Laubengayer, J. Amer. Chem. Soc. 90 (1968) 3173; (4) G. B. Sakharovskaya, N. N. Korneev, A. F. Popov, S. Z. Snegova, A. F. Zhigach and M. V. Sobolewskii, Brit. 1, 319, 746 (Ch. CO8g) June 6, 1973, Appl. 6621/71, March 11, 1971; (5) M. Aoyagi, T. Vada, Y. Tadokoro and S. Horikivi, Jpn. Kokai Tokkyo Kono 79, 64, 600 (Cl. CO8g 79/10) May 24, 1979, Appl. 77/131,909 Nov. 1, 1977: (6) J. Herwig, Dissertation, Hamburg University (1979); (7) H. J. Vollmer, Dissertation, Hamburg University (1980); (8) A. Wolinska, J. Organomet. Chem. 234 (1982) 1; and M. Boleslawski and J. Serwatowski, J. Organomet. Chem. 254 (1983) 159.

These methods bring the water and the aluminum alkyls into direct contact with each other. They are intended for the preparation of small quantities for catalytic investigations. The methods of preparation differ with respect to the carrier for the water. Vandenberg (1) reacts aluminum alkyls and water without a carrier. Sakharovskaya et al. (4) use a $N_2$ stream as entrainer for the water required for the reaction. In Hamburg the molecular-sieve method (6), (7) was developed. In this method, a molecular sieve loaded with water serves as carrier or source of water.

The direct method poses the risk of a slight "running away" of the reaction. The water, introduced into the reactor by means of a carrier, is bound to the latter only physically and therefore readily released, which renders a controlled reaction difficult.

When the water required for the partial hydrolysis of aluminum alkyls is introduced chemically combined in the form of salt hydrates, slow liberation of the water of crystallization, and hence a quiet reaction, are assured. This reasoning has led to the water-of-crystallization method, published by (10) G. A. Razuvajev, J. A. Sangolov, J. J. Nelkenbaum and K. S. Minsker, Jzw. Akad. Navk. SSR, Ser.Chim. 19 (1975) 2547; (11) H. Hahnsen, Thesis, Hamburg University (1980); and (12) S. R. Rafikov, K. S. Minsker, J. A. Sangalov and J. J. Nelkenbaum, USSR Patent 566,844, C. A. 87 (1977) 152373h.

Further methods of preparation are designed to obtain the Al-O-Al linkage through appropriate choice of organoaluminum compounds such as dialkylaluminum chloride and lithiumdialkyl aluminate, alkoxyaluminum dichloride or methylmethoxyaluminum chloride, and methylaluminum chloride or ethylaluminum chloride. These methods have been published by (13) H. Tani, T. Araki, N. Oguni, T. Aoyoagi and N. Ueyama, J. Pol. Sci. Po. Lett. (8) 4 (1966) 97; (14) H. Tani, T. Araki, N. Ogunbi, T. Aoyoagi and N. Ueyama, J. Amer. Chem. Soc. 89 (1967) 173; (15) N. Ueyama, T. Araki and H. Tani, Inorg. Chem. 12 (1973) 2218; (16) W. Kosinska, K. Zardecka, A. Kunicki, M. Boleslawski and S. Pasynkiewicz, J. Organomet. Chem. 153 (1978) 281; and (17) W. Kosinska, A. Kunicke, M. Boleslawski and S. Pasynkiwicz, J. Organomet. Chem. 161 (1978) 289.

Aluminum oxanes can also be prepared by reacting aluminum trialkyls with PbO, as described by (18) M. Boleslawski and S. Pasynkiewicz, J. Organomet. Chem. 43 (1972) 81.

Lastly, the water-of crystallization method was improved by the use of predehydrated aluminum sulfate as a source of water, as described by (21) H. H. Hahnsen, Dissertation, Hamburg University (1984) and (22) Kaminsky and Hahnsen, German published patent application OS 32 40 383.

However, predehydration is expensive, and any insoluble or sparingly soluble aluminum oxane which may form remains undetected and is discarded with the crystal slurry. It is nearly impossible to establish a mass balance for the reaction.

Consequently, aluminum oxanes have not been readily available in moderately large quantities up to now, and their structure has therefore not been clarified, nor have fields of application been developed for them.

The object of the present invention is to develop a process for producing aluminum oxanes which can be carried out also on a commercial scale and can be expected to permit a reduction in the cost of catalyst systems based on aluminum oxanes, the development of rare-earth-alloy oxanes with specific aluminum contents, and the use of aluminum oxanes and aluminum-containing metal oxanes as catalyst supports and as starting materials for specialty ceramics.

In the underlying efforts to master the direct reaction of an aluminum trialkyl, preferably aluminum trimethyl, with water in an inert solvent such as toluene, a number of surprising facts came to light:

(A) On a bright surface of ice immersed in a solution of trimethylaluminum, an evolution of gas occurs that is more or less pronounced as a function of temperature. It is found that directly on the surface the temperature is higher than in the vicinity and at the core. The reaction then either accelerates to the point of going out of control or comes to an end. The ice surface then has a dull appearance.

(B) When an ice surface on which the reaction has come to an end is scoured bright with a steel wire in some areas, an evolution of gas will again occur there, and at moderately high temperatures even violent gas eruptions. However, the evolution of gas will subside quickly. The process ca be repeated time and again at temperatures between 200 and 250 K.

(C) When a sheet of ice on whose surface no further reaction has been observed in a solution of trimethylaluminum is broken in the solution, gas will evolve mainly at the fractures.

(D) When tiny lumps of ice are used, the gas bubbles which form, and which do not readily separate from the lumps of ice, will lift the latter to the surface of the solution. They will collect in a layer of foam. There an insoluble material which envelops the lumps of ice will form. This is an aluminum oxane which contains less than a methyl group per aluminum atom.

(E) If the alkylaluminum solution is recirculated by means of a glandless gear pump and a focused powerful jet is directed below the surface of the solution onto the surface of the ice introduced, a reaction evidently takes place at the point where the jet impinges: The ice becomes bright and sustains a depression.

The following teaching is arrived at on the basis of these facts:

(a) It is necessary to create a well-defined ice surface in a solution of alkylaluminum and keep it reactive by erosive action.

(b) The reactive surface must be subjected to a sufficiently strong stream for aluminum oxane which formed to be carried away and not to be able to react with more water from the ice surface to form insoluble low-alkyl aluminum oxane.

(c) The formation of small ice particles which are carried by gas bubbles into the foam layer should be prevented, or then the circulation of the liquid should be directed so that the particles are drawn from the foam layer into the liquid.

(d) To prevent the formation of insoluble aluminum oxane, it is advisable to use an excess of alkyl (based on the available water).

(e) The gas evolution starting at the surface should nor be so strong that the alkylaluminum solution is unable to constantly flood the surface and remove the soluble reaction products. This may be controlled through the temperature of the surface and of the ice. It is therefore advisable to be able to control the temperature of the ice independently of the temperature of the surrounding trialkyl solution. This can be accomplished within certain limits by placing the ice on a cooled dish in the solution and cooling the dish through a coolant loop of its own, another coolant loop being provided for holding the solution at the desired temperature.

The invention is broadly directed to a process for producing aluminum oxane by subjecting frozen water in a solution of trialkylaluminum in hydrocarbons to erosive action. In particular, the invention is a process for producing methylaluminum oxane which is characterized in that frozen water in a solution of trimethylaluminum in hydrocarbons is subjected to erosive action which is exerted by mechanical action or by one or more intensive liquid jets of the reaction solution sweeping over the surface of the frozen water.

The mechanical action is preferably exerted by means of rapidly rotating impact blades or of scouring and scraping tools on a surface of the frozen water.

One embodiment of the process is characterized in that a 5 to 15% solution of trimethylaluminum in toluene or cumene is used as the solution of trimethylaluminum in hydrocarbons.

Another embodiment of the process is characterized in that the velocity of erosion and/or the velocity of cooling are/is controlled so that an internal temperature of 250 K. is not exceeded, that a temperature of from 220 to 240 K. is preferably obtained, and that the temperature is not below 190 K.

A further embodiment of the process is characterized in that the velocity of erosion and/or the velocity of cooling are/is controlled so that, at an internal temperature of less than 250 K., not more than 0.25 mole of water per liter of solution is eroded and reacted per hour.

Still another embodiment of the process is characterized in that the quantities of water and of trimethylaluminum are sized so that at the end of the reaction, that is, after the frozen water has been used up or the erosion action has ceased, unreacted trimethylaluminum is still present, preferably in an amount of from 10 to 50 g per liter.

A further embodiment of the process is characterized in that the desired excess of trimethylaluminum is introduced initially and then maintained by being replenished at a rate of which the trimethylaluminum is consumed.

The implementation of this process is described by way of example in a number of operating instructions in the examples. The latter demonstrate that the inventive operating procedure prevents the formation of insoluble aluminum oxanes almost completely and further permits the immediate reuse of the unreacted alkylaluminum and of the solvent in the next batch. In a series of batches, both the water, introduced in the form of ice, and the alkylaluminum are therefore converted 100%, with yields of over 90% soluble aluminum oxane and correspondingly little insoluble aluminum oxane. No byproducts are formed.

EXAMPLE 1

To a one-liter agitated glass autoclave which is equipped with a temperature-control jacket and whose cover is provided with a glandless agitator with a magnetic clutch, a temperature sensor, closeable charging openings and gas connections and can also be cooled, and on whose agitator shaft a conventional impeller and, in addition, cutter blades from a kitchen blender are mounted (see FIG. 1), a solution of 360 ml of toluene and 40 ml (corresponding to 400 millimoles) of trimethylaluminum are charged under a protective gas (countercurrent argon). After cooling to $-80°$ C., 3.76 g of ice, cooled to $-80°$, is thrown in.

The charging opening is then closed and the connection to the gas measuring and collecting system is opened through a valve. Then the agitator is started and the agitating speed is increased until the ice added is chopped. After a slight gas-evolution surge, the reaction sets in with a rate of gas evolution of from 1 to 2 liters per hour. As soon as the gas-evolution rate drops, the speed of rotation is increased and the temperature raised by regulating the thermostat controlling the cooling jacket.

After from 8 to 9 liters of gas have been collected at room temperature, the thermostat is turned off. The temperature is then allowed to rise to room temperature. A total of from 9.5 to 10 liters is collected at room temperature. This is the theoretical quantity for the reaction of 3.76 ml of water with an excess of trimethylaluminum. The nearly colorless solution obtained is forced through a G4 sintered filter from the autoclave into a receiver, degassed, and freed from excess trimethylaluminum and toluene by condensation in a high vacuum.

There remain from 16 to 17 g of a spongy, glassy material that can be crushed to a white powder. This material ignites spontaneously in air and dissolves readily in benzene, toluene and cumene as well as in other aromatic compounds, sparingly in methylcyclopentane and methylcyclohexane, and hardly at all in alkanes.

EXAMPLE 2

The agitated autoclave mentioned in Example 1 is suspended in the cold bath. In the interior of the autoclave, a temperature lower than −60° C. is obtained. Solvent, and trimethylaluminum in the solvent, are then carefully charged in such a way that nearly pure solvent overlies a relatively concentrated solution at the bottom of the autoclave. With the agitator upright, the necessary ice is added to the liquid, the autoclave is closed, and the connection to the gas-measuring and gas-collecting system is established.

Low-speed agitation is now started, which causes the sudden initiation of the reaction. From a batch with 40 ml of trimethylaluminum, 360 ml of toluene and 3.76 g of ice, up to 5 liters of methane per hour are generated, which can just barely be controlled. However, so much foam may form that reaction mass is forced out through the gas discharge line. A receiver capable of being cooled should therefore be interposed between the autoclave and the gas-collecting vessel.

As soon as the gas-evolution rate drops, the speed of agitation is increased so that erosion and size reduction of the ice particles set in. The speed of agitation is increased at intervals so that foaming can just be controlled, which is the case at a gas-evolution rate of from 3 to 4 liters per hour. When the agitation speed cannot be increased further and the gas-evolution rate markedly decreases (at which point about 8 liters of gas will have been generated; if less has been generated, extra care is indicated), the temperature is allowed to rise to room temperature over a period of from one and one-half to two hours by withdrawing the liquid coolant but agitating vigorously, with the reaction then going to completion. The spent solution is forced through a G4 sintered filter into a receiver.

On the filter there are from 2 to 3 g of a substance which is insoluble in aromatic compounds and has an aluminum/methyl ratio of between 1 and 2. The filtrate is treated as in Example 1 and yields approximately 12 g of methylaluminum oxane soluble in aromatics.

EXAMPLE 3

(Comparative Example)

To a one-liter three-necked flask, 360 ml of absolute (anhydrous) cumene and 40 ml of pure trimethylaluminum are charged. The flask is equipped with a KPG agitator, a protective-gas inlet and a gas outlet as well as a temperature-controlled dropping funnel. The three-necked flask is cooled to −40° C. by immersion in a cold bath.

In a separate vessel, 4 ml of water is suspended as finely as possible in 50 ml of cumene by means of an Ultra-Turrex agitator while being cooled to −30° C. Tiny and very thin lamellar ice crystals are so obtained which settle at a temperature above −30° C. and float at a temperature below −30° C. The suspension is transferred to the dropping funnel, brought to a temperature of −20° C., and added in small portions to the previously introduced alkyl. The reaction sets in immediately and methane and a fine foam are formed along with small amounts of a white solid (insoluble aluminum oxane).

If foam formation becomes too violent or the rate of gas evolution exceed 0.3 liters per minute with such a batch, the rate of reaction is reduced by immersing the three-necked flask for a short time in the cold bath beneath it. Within one hour, all water in the form of the suspension has been added and about 10 liters of gas have been generated. At that point, the temperature in the flask should be about −20° C. Over a period of one hour, the temperature is allowed to rise to room temperature with evolution of a little gas.

When from 9 to 10 liters of gas have evolved in a controlled manner, a violent reaction will occur only with gross carelessness. As the temperature rises, the solution becomes perfectly clear and bright with slow agitation, and some insoluble aluminum oxane or also aluminum oxide settles out. The batch is drawn off through a G4 sintered filter and the filtrate is worked up to soluble aluminum oxane.

The filter cake amounts to from 3 to 6 g and with access of water or air is apt to decompose violently. From the filtrate, from 13 to 16 g of crude product is obtained which dissolves readily in toluene and when used as a catalyst component for soluble Ziegler catalysts exhibits the usual activity. It contains minor amounts of free trimethylaluminum.

The mixture of cumene and excess trimethylaluminum can be used as starting solution for a new batch, for which purpose it need only be enriched with trimethylaluminum to a content of 40 ml per 400 ml of solution.

EXAMPLE 4

A tubular reactor with an inside diameter of approximately 80 mm and a capacity of 2.5 liters which is equipped with a cooling jacket is closed with a flange at the top and the bottom. From each flange an agitator shaft with a magnetic clutch projects into the reactor. The hemispherical lower mixing space is filled with cumene and is in exchange with the contents of the reactor only through the sealing clearance. A cooled annular plate is mounted on the lower flange in such a way that the horizontally disposed annular plate surrounds the vertical agitator shaft so that the latter is able to move without being encumbered by the annular plate.

After the reactor has been evacuated and filled with argon, water is introduced into the depression in the annular plate and deep-frozen by turning on the cooling system of the annular plate. Onto the lower shaft, above the annular plate, a milling cutter is now placed which by means of a pin is guided in a slot in the agitator shaft. As the agitator shaft rotates, the milling cutter consequently exerts a grinding action on the surface of the deep-frozen ice, regardless of its thickness.

The agitator shaft projecting from the upper flange, and the wall-scraping agitator mounted on it, serve to thoroughly mix the liquid content of the reactor and can be rotated and controlled independently of the lower agitator shaft.

The annular plate is now filled with 7.5 g of water and then cooled to from 205 to 210 K. The free ice surface obtained in this case measures 41 $cm^2$, due to the construction.

On completion of the freezing of the water, 800 ml of precooled toluene (or cumene) is introduced. The liquid level is about 10 cm above the agitator plate. The wall-scraping agitator on the upper shaft dips into the liquid. By charging the cooling jacket, the introduced liquid is also cooled to 210 K. To the cooled liquid there is now added 80 ml, corresponding to 60 g, of trimethylaluminum, a portion of which dissolves while another portion freezes out and overlies the liquid as a crystal slurry. After providing for pressure equalization, establishing a connection to a gas meter through a blubber valve and buffer vessel, and introducing a thermoelement into the liquid, the cutter head is first set into motion through the lower agitator and then the dissolved and suspended trimethylaluminum is dispersed in the inert liquid by means of the upper agitator.

At the annular plate, an evolution of tiny gas bubbles sets in. By reducing the cooling, the temperature is allowed to rise to 220 to 230 K., with the rate of gas evolution then reaching values of up to 12 liters per hours. After three hours, 18 liters of gas have evolved. (Room temperature.) Over a period of another hour, the temperature is allowed to rise to room temperature, with a further 2 liters of gas being generated. Few flocs precipitate in the solution. The solution is forced into a glass flask under argon. The solvent is condensed off under vacuum and after being replenished can be used along with any trimethylaluminum present for the next batch without being worked up further. Residue: 27 g methylaluminum oxane with traces of trimethylaluminum.

We claim:

1. A process for producing methylaluminum oxane, which comprises subjecting frozen water in a solution of trimethylaluminum in hydrocarbons to erosive action exerted by mechanical action on the surface of the frozen water or by one or more intensive liquid jets of the solution sweeping over the surface of the frozen water.

2. A process as defined in claim 1, wherein said mechanical action is exerted by rapidly rotating impact blades.

3. A process as defined in claim 1, wherein said erosion is effected by means of scouring and scraping tools on a surface of the frozen water.

4. A process as defined in claim 1, wherein a 5 to 15% solution of trimethylaluminum in toluene or cumene is used as the solution of trimethylaluminum in hydrocarbons.

5. A process as defined in claim 1, wherein the velocity of erosion, the velocity of cooling or both are controlled so that an internal temperature from about 190 to 250 K. is obtained.

6. A process as defined in claim 5, wherein the velocity of erosion, the velocity of cooling or both are controlled so that, at an internal temperature of less than 250 K., not more than 0.25 mole of water per liter of solution is eroded and reacted per hour.

7. A process for producing an aluminum oxane, which comprises subjecting frozen water in a solution of trialkylaluminum in hydrocarbons to erosive action.

8. A process as defined in claim 7, wherein said aluminum oxane is methylaluminum oxane.

9. A process as defined in claim 7, wherein said frozen water is in a solution of trimethylaluminum in hydrocarbons.

10. A process as defined in claim 7, wherein said erosion controls through mechanical action exerted on the frozen water.

11. A process as defined in claim 10, wherein said mechanical action is exerted by rapidly rotating impact blades.

12. A process as defined in claim 10, wherein said erosion is effected by means of scouring and scraping tools on a surface of the frozen water.

13. A process as defined in claim 7, wherein said erosion is effected through one or more intensive liquid jets of the solution sweeping over the surface of the frozen water.

14. A process as defined in claim 9, wherein a 5 to 15 weight % of trimethylaluminum in toluene or cumene is used as the solution of trimethylaluminum in hydrocarbons.

15. A process as defined in claim 7, wherein the velocity of erosion, the velocity of cooling or both are controlled so that an internal temperature from about 190 to 250 K. is obtained.

16. A process as defined in claim 15, wherein said temperature is from about 220 to 240 K.

17. A process as defined in claim 15, wherein the velocity of erosion, the velocity of cooling or both are controlled so that, at an internal temperature of less than about 250 K., not more than about 0.25 mole of water per liter of solution is eroded and reacted per hour.

18. A process as defined in claim 9, wherein the quantities of water and of trimethylaluminum are sized so that after the frozen water has been used up or the erosive action has ceased, unreacted trimethyaluminum is still present.

19. A process as defined in claim 18, wherein said unreacted trimethylaluminum is present in an amount of about 10 to 50 g per liter.

20. A process as defined in claim 9, wherein an excess of trimethylaluminum is introduced initially and then maintained by replenishment at a rate at which the trimethylaluminum is consumed.

* * * * *